(12) United States Patent
Gao et al.

(10) Patent No.: US 6,218,507 B1
(45) Date of Patent: Apr. 17, 2001

(54) SYNTHETIC PEPTIDES FOR THE DETECTION OF TRIMETHYLAMINE (TMA) AND THEIR DETECTION METHOD AND DEVICE

(75) Inventors: Heau-Shan Gao; I-Nan Chang; Tzong-Zeng Wu; Ya-Ling Liao; Sung-Sheng Hsiung, all of Taipei (TW)

(73) Assignee: Development Center for Biotechnology, Taipei (TW)

( * ) Notice: Subject to any disclaimer, the term of this patent is extended or adjusted under 35 U.S.C. 154(b) by 0 days.

(21) Appl. No.: 09/143,708

(22) Filed: Aug. 28, 1998

(30) Foreign Application Priority Data

Nov. 26, 1997 (TW) ................................. 86117774

(51) Int. Cl.$^7$ ................................. C07K 7/06; C07K 7/08
(52) U.S. Cl. ................. 530/327; 530/328; 530/329; 514/14; 514/15; 514/16; 514/17
(58) Field of Search ................................. 530/328, 329, 530/327; 514/14, 15, 16, 17

(56) References Cited

FOREIGN PATENT DOCUMENTS

WO92/17585  * 10/1992  (WO) .
WO94/05695     3/1994  (WO) .

OTHER PUBLICATIONS

Ngo et al., 'Computational Complexity, Potein Structure Prediction, and the Levinthal Paradox,' The Protein Folding Problem and Tertiary Structuer Prediction. Ed. K. Merz and L. Le Grand. BirkHauser, Boston MA. pp. 491–495, 1994.*
Rudinger, J. (1976). Peptide Hormones (ed. J.A. Parsons). University Park Press. Baltimore. pp. 1–7, 1976.*
Buck et al., "A Novel Multigene Family May Encode Odorant Receptors: A Molecular Basis for Odor Recognition", Dept. of Biochemistry and Molecular Biophysics, vol. 65, (175–187, Apr. 5, 1991).

Xiao S., "Abstract", *Database WPI*, Section Ch, Week 199531, Derwent Publications Ltd., London, 1995.
Tokyo Shibaura Electric Co., "Abstract", *Database WPI*, Section Ch, Week 197384, Derwent Publications Ltd., London, 1978.
Application of PZ–Olfactory Biosensor for the Quality Assesments of Sorghum Liquor, *Analytical Sciences*, vol. 7, Supplement, pp. 867–870, 1991.
A Novel Multigene Family May Encode Odorant Receptors: A Molecular Basis for Odor Recognition, *Cell*, vol. 65, pp. 175–187, 1991.
Nonaka, J. et al., "Bulletin of the Japanese Society of Scientific Fisheries", vol. 58, pp. 2039–2044 (1967).
Siminhoff, M.L. et al., "The New England Journal of Medicine", vol. 297, pp. 132–135 (1977).
Lancet, D., "Annual Review of Neuroscience", vol. 9, pp. 227–255 (1986).
Buck. L. and Axel, R., "A Novel Multigene Family May Encode Odorant Receptors: A Molecular Basis for Odor Recognition", vol. 65, pp. 175–187 (1991).
Wu, T.Z. and Wan, H.H., "Analytical Science" vol. 7, Supplement, pp. 867–870 (1991).

* cited by examiner

*Primary Examiner*—Christopher S. F. Low
*Assistant Examiner*—Anish Gupta
(74) *Attorney, Agent, or Firm*—Christensen O'Connor Johnson Kindness PLLC

(57) ABSTRACT

The present invention describes a peptide and analogues thereof, which is a fragment of an olfactory receptor protein capable of selectively binding to trimethylamine so that they are useful for detecting trimethylamine.

The present invention further describes a method and a device for detecting trimethylamine by using the peptide and the analogues thereof.

2 Claims, 6 Drawing Sheets

US 6,218,507 B1

SYNTHETIC PEPTIDES FOR THE DETECTION OF TRIMETHYLAMINE (TMA) AND THEIR DETECTION METHOD AND DEVICE

RELATED APPLICATIONS

The present application claims benefit of ptiority from Taiwanese Application No. 86117774, filed on Nov. 26, 1997, the benefit of which is hereby claimed under 35 U.S.C. § 119.

FIELD OF THE INVENTION

The present invention is directed to a peptide and the analogues thereof capable of detecting trirnethylamine, and a method and a device for detecting trimethylamine using the peptides.

BACKGROUND OF THE INVENTION

Trinethylamine (TMA) is an offensively smelling gas having an irritating, fishy and ammonia-like odor, and is a listed substance under restriction control according to the regulations on the air pollution control act. With respect to the quality control in food industry, the amount of volatile alkali substance such as trimethylanine will increase during the putrefaction of seafood (e.g. fish and shrimp). Therefore, the level of putrefaction of seafood can be indicated by the detection of the amount of trimethylamine present (Nonaka, J. et al., Bull. Japan Soc. Sci. Fish, Vol. 58, pp. 2039–2044, 1967). With respect to medical diagnosis, an increase of concentration of trimethylamine in the breath of patients can be used as an index of virernic diseases. (Siminhoff, M. L. et al., N. Engl. J. Med. Vol. 297, pp. 132–135, 1977). Therefore, the techniques for detecting trimethylamine are applicable in the fields of environmental protection, food industry and medical diagnosis.

In general, trimethylamine is determined by, for instance, acid titration and instrumental analysis such as gas chromatography, and mass spectrometry. However, such methods have some disadvantages, such as which involve complicated operation procedures, and are time-costing and difficult to analysis.

In view of the fact that various odorant molecules are identified by olfactory organs due to the binding of the odorant molecules and the receptor proteins on olfactory cilia (ancet D., Annu. Rev. Neurosci, Vol. 9, pp. 227–255, 1986). In 1991, the gene family of the olfactory receptor proteins were cloned and characterized. The protein sequences of the odorant receptors were determined by Buck and Axel (Buck, L. and Axel, R, Cell Vol. 65, pp. 175–187, 1991). In addition, a device for identifying the aroma of the wine through the binding by an olfactory receptor protein of a bullfrog was published (Wu, T. Z., and Wan, H. H., Analytical Science Vol. 7, Supplement, pp.867–870, 1991).

SUMMARY OF THE INVENTION

The present invention provides a peptide and the analogues thereof capable of detecting trimethylamine, which is a fragment of an olfactory receptor protein. The disadvantages occurring in the prior art have been eliminated by the invention.

An object of the present invention is to provide a peptide capable of detecting trimethylamine, which comprises the following amino acid sequence:

Cys-Pro-Ser-Ala-Asn-Asn-Ser-Thr-Val-Lys-Glu  (SEQ ID) NO.1).

Another object of the present invention is to provide an analogue of the peptide, which comprises one of the following sequences:

Cys-Pro-Ser-Ala-Asn-Asn-Ser-Thr    (SEQ ID NO.2);

Cys-Pro-Ser-AIa-Asn-Asn             (SEQ ID NO.3);

and

Cys-Asn-Ser-Thr-Val-Lys-Glu         (SEQ ID NO.4).

A further object of the invention is to provide a peptide capable of detecting trimethylamine and binding to a piezo-electric crystal, which comprises the peptide as defined above and a spacer binding the carboxy-terniinal of the peptide to a piezoelectric crystal. The preferred embodiments include as follows:

Cys-Pro-Ser-Ala-Asn-Asn-Ser-Thr-Val-Lys-Glu-Gly-Cys-Gly    (Peptide I, SEQ ID No. 5);

Cys-Pro-Ser-Ala-Asn-Asn-Ser-Thr-Gly-Cys-Gly                (Peptide II, SEQ ID No. 6);

Cys-Pro-Ser-Ala-Asn-Asn-Gly-Cys-Gly                        (Peptide III, SEQ ID No. 7); and Cys-Asn-Ser-Thr-Val-Lys-Glu-Gly-Cys-Gly                    (Peptide IV, SEQ ID No. 8).

In preferred embodiments, the spacer is -Gly-Cys-Gly, Ala-Cys-Ala, Ala-Cys, Gly-Cys- or Cys.

A further another object of the invention is to provide a method for detecting trimethylamine.

Also, the present invention provides a device for detecting trimethylamine.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

Figure 1:
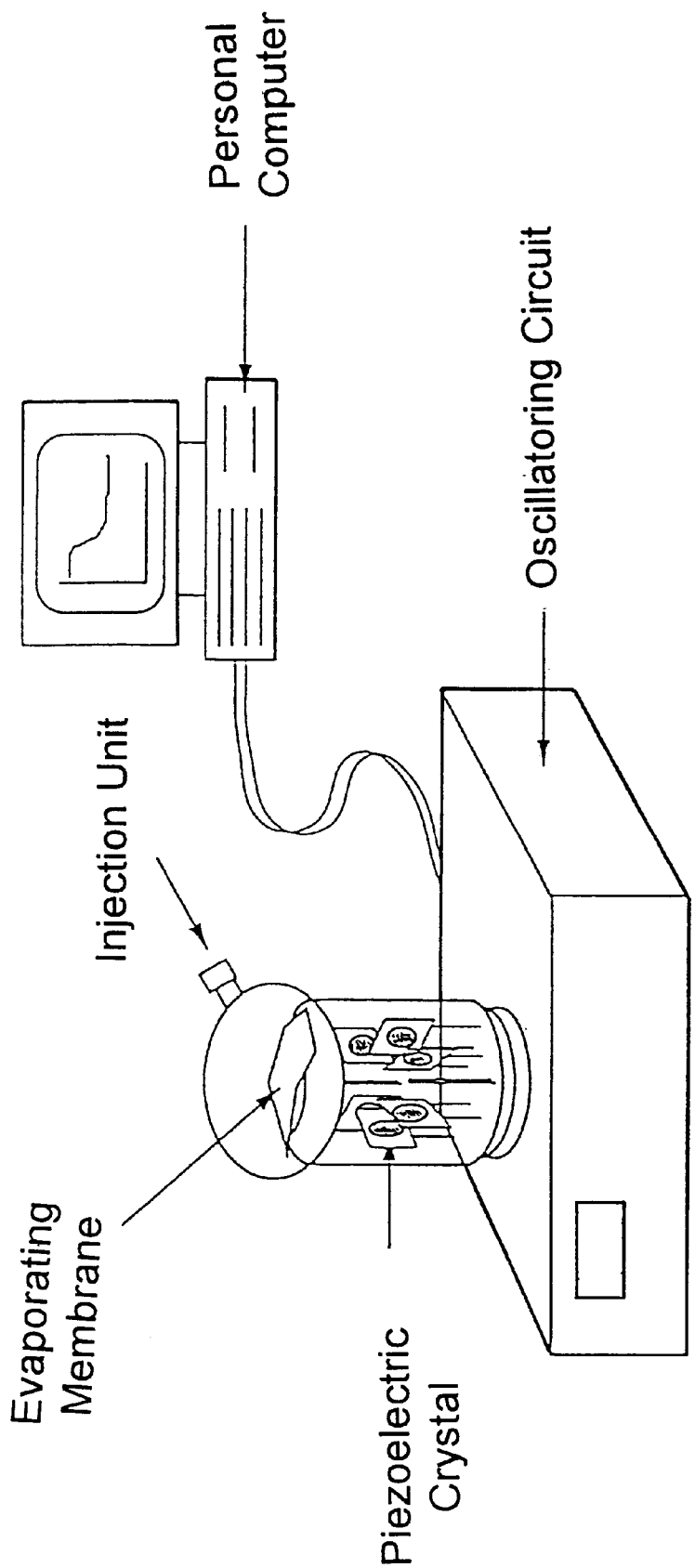
FIG. 1 is a schematic drawing showing an piezoelectric crystal gas sensor device.

| NOTATION OF ABBREVIATION | | | |
|---|---|---|---|
| Ala (A): | Alanine | Arg (R): | Arginine |
| Asn (N): | Asparagine | Asp (D): | Aspartic acid |
| Cys (C): | Cysteine | Glu (E): | Glutamic acid |
| Gly (G): | Glycine | Leu (L): | Leucine |
| Lys (K): | Lysine | Phe (F): | Phenylalanine |

-continued

| NOTATION OF ABBREVIATION | | | |
|---|---|---|---|
| Pro (P): | Proline | Ser (S): | Serine |
| Thr (T): | Threonine | Val (v): | Valine |

DETAILED DESCRIPTION OF THE PREFERRED EMBODIMENT

The present invention provides a peptide capable of detecting trimethylamine, which contains the following sequence:

Cys-Pro-Ser-Ala-Asn-Asn-Ser-Thr-Val-Lys-Glu   (SEQ ID NO. 1).

The peptide of the present invention is obtained by screening the amino acid sequence fragments capable of selectively binding to trimethylamine from a natural olfactory receptor protein. The present invention also provides the analogues which are optionally modified by addition or deletion of amino acids on the peptides. Analogs could be the peptides that substitutions of amino acid residues or the peptides that contain insertion and/or deletion of amino acids in the peptide of SEQ ID NO. 1.

The preferred embodiments of the analogues of the invention include:

Cys-Pro-Ser-Ala-Asn-Asn-Ser-Thr   (SEQ ID NO.2);

Cys-Pro-Ser-Ala-Asn-Asn   (SEQ ID NO.3);

and

Cys-Asn-Ser-Thr-Val-Lys-Glu   (SEQ ID NO.4).

The invention also provides a peptide capable of detecting trimethylamine and binding to a piezoelectric crystal, which comprises the peptide as defined above and a spacer binding the carboxy-terminal of the peptide to a piezoelectric crystal.

In the invention, a spacer is used to allow the peptide of the invention to immobilize on the surface of a piezoelectric crystal electrode. The spacer includes a peptide fragment having a sequence such as -Gly-Cys-Gly, Ala-Cys-Ala, Ala-Cys, Gly-Cys- or Cys-, which is added at the carboxy terminal of the peptide. The spacer provides a thio group of cysteine on the terminal of the peptides to form a chemical adsorption between the peptide and the surface of the piezoelectric crystal electrode so that the peptide will be immobilized to the surface of the piezoelectric crystal electrode. The most preferred embodiment of the spacer is -Gly-Cys-Gly-.

In preferred embodiments of the invention, the peptides capable of detecting trimethylamine and binding to a piezoelectric crystal are:

Cys-Pro-Ser-Ala-Asn-Asn-Ser-Thr-Val-Lys-Glu-Gly-Cys-Gly   (Peptide I, SEQ ID NO. 5);

Cys-Pro-Ser-Ala-Asn-Asn-Ser-Thr-Gly-Cys-Gly   (Peptide II, SEQ ID NO. 6);

Cys-Pro-Ser-Ala-Asn-Asn-Gly-Cys-Gly   (Peptide III, SEQ ID NO. 7); or

Cys-Asn-Ser-Thr-Val-Lys-Glu-Gly-Cys-Gly   (Peptide IV, SEQ ID NO. 8).

The peptide and analogues thereof according to the invention could be in cyclic, partially or totally cyclic form. Alternatively, it could be the polymer, such as that having one or more repeating amino acid units. It could be the polychained peptide containing branch chains on the central nucleus. It could be the peptides that substitutions of amino acid residues or the peptides that contain insertion and/or deletion of amino acids in the peptide I to IV.

The peptide of the present invention is prepared by any conventional technology for peptide synthesis. For instance, it can be prepared by a solid phase peptide synthesis, i.e. by binding a C-terminal amino acid of a peptide to a insoluble solid support via a binding of a carboxylic acid group, subjecting to the coupling and deprotection, and adding the amino acids to the solid support according to the design of the amino acid sequences. The synthesized peptide is then cleaved and separated from the solid support as described in Example 1.

According to the present invention, the peptide can also be synthesized by using known techniques such as liquid peptide synthesis, enzymatic synthesis, or recombinant DNA technology. Using suitable polymerases and/or microorganisms, the desired peptide can be expressed by a microorganism into the genome of which the DNA sequence coding for the desired peptide is incorporated.

Figure 5:
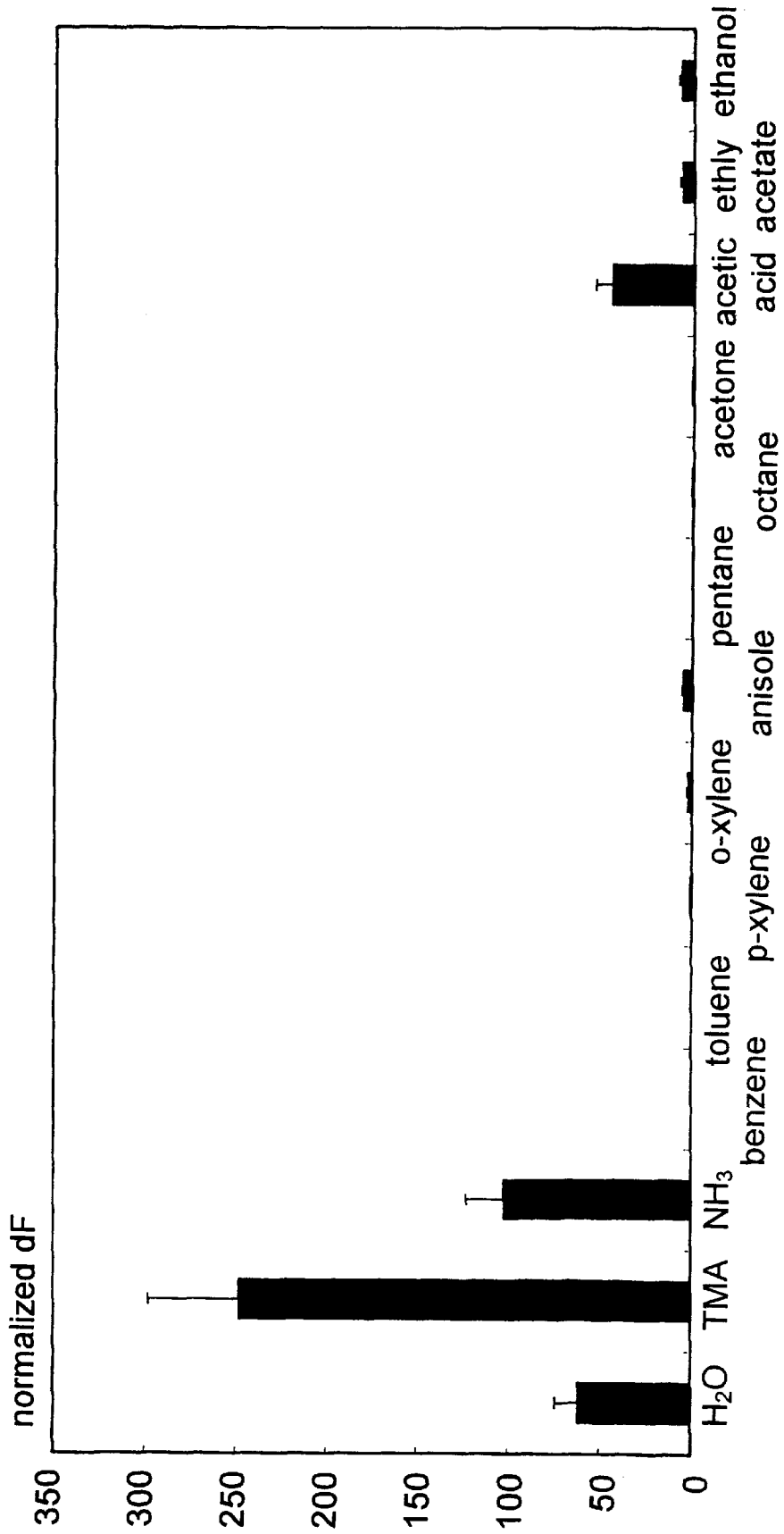
FIG. 5 is a normalized dF showing the responses of various gases such as trimethylamine using Peptide I as a detector.

The peptides of the invention have a selective adsorption to trimethylamine, but a less response to other odor gases such as ammonia, water, acetic acid, acetone, ethyl acetate, ethanol, aromatic and aliphatic compounds, as shown in Example 4, FIG. 5 and Table 1.

The present invention also provides a method and a device for detecting trimethylamine by using the peptides of the invention.

The principle for the detection of a gas sample through a piezoelectric crystal is that the vibration frequency of the piezoelectric crystal will decrease as the weight of a substance adsorbed on the surface of the piezoelectric crystal increases. Since there is a specific affinity between trimethylamine and the film of the peptide of the invention which is coated on the surface of the electrode on the piezoelectric crystal, the vibration frequency will decrease as the weight of the adsorption of trimethylamine by the peptide on the crystal increases. In view of the change of vibration frequency measured by a resonance frequency meter, the level of trimethylamine in a given sample can be detected.

Therefore, the invention provides a method for detecting trimethylamine, which is characterized by the steps of coating the peptide of the invention on an element for signal conversion, and detecting the signal change due to the increase of the adsorption of trimethylamine by the peptide on the surface of the element.

In one embodiment of the invention, a piezoelectric crystal is used as an element for signal conversion, and the peptide capable of detecting trimethylamine is directly coated on an electrode of the piezoelectric crystal. The electrode may be made from a chemically inert material including a chemically inert metal. The piezoelectric crystal may be made from quartz, polyvinylene difluoride (PVDF), lithium nicobate, and aluminum nitride etc. In a preferred embodiment, a quartz crystal and a gold electrode are used.

In other embodiments of the invention, the elements for signal conversion include similar detection elements, such as an mass-sensitive element for signal conversion. For instance, when detected by a high frequency Surface Acoustic Wave (SAW), the detection element can be made from the materials similar to piezoelectric crystal materials, such as quartz, polyvinylene difluoride (PVDF), lithium nicobate, and aluminum nitride. When detected by Surface Plasma Resonance (SPR) technology, the detection element can be a total-reflexible optical material coated with a heavy metal film, wherein the total-reflexible optical material includes such as glass, quartz, polystyrene, polycarbonate and poly (methyl 2-methylacrylate) (PMMA), and the heavy metal can be gold, silver or cadmium. When detected by capacitance, an insulating material such as glass, ceramics or high molecular weight polymers should be used and detection element can be made from a conductive material such as gold, silver, titanium and conductive polymer. When detected by electrical resistance, the peptide of the invention should be doped in a highly conductive polymer such as polypyrrole, polythiophene or polyacetylene etc. When detected by reflectormetry, the detection element can be made from a reflexible optical material such as silicon, glass and metal, etc. When detected by eflipsometry, the detection element can be made from a reflexible optical material such as silicon, glass, and metal.

The peptide of the invention can be coated on an element for signal conversion through either a physical adsorption or a chemical reaction. In a preferred embodiment, the peptide of the invention binding to a protein or a polymer is coated on an element for signal conversion, wherein the polymer is selected from the group consisting of a protein, a polypeptide, a natural or synthetic water-soluble polymer containing repeating units of amino acids or saccharides, a polymer of hydrogel. Alternatively, the peptide of the invention can be coated on an element for signal conversion through a linkage of alkylthiol or lipid.

One preferred embodiment of the invention is a sensor crystal coated with the peptide of the invention to provide a device for quickly detecting trimethylamine.

The following examples together with the accompanying drawings are offered to aid in understanding of the purposes, methods, characteristics and concepts of the present invention, but not to be construed as limiting the scope thereof

EXAMPLES

Example 1 The Solid Phase Synthesis of the Present Peptide

According to the Merrifield solid phase peptide synthesis methodology, peptide I of the following formula:
-Cys-Pro-Ser-Ala-Asn-Asn-Ser-Thr-Val-Lys-Glu-Gly-Cys-Gly (Peptide I) (SEQ ID NO:5) was prepared by stepwise covalent bonding of L-amino acids in a designed sequence in a direction from the carboxy terminal toward amino terminal to a solid support of polystyrene resin by using an Fmoc protecting group synthesis strategy. Such a sequentially covalent bonding of amino acids comprises the steps of deprotecting the protection group from the peptide, subjecting the deprotected peptide to a coupling reaction to add a desired amino acid sequence and then cleaving and separating the resulting peptide from the peptide-resin. The peptide-resin was treated as follows:

(a) The peptide-resin was immersed in N-methylpyrrolidine (NMP) for 10 minutes;

(b) The peptide-resin was treated twice by N-methylpyrrolidone (NMP) containing 40% of piperidine for 3 and 8 minutes respectively to remove the amino protecting group thereon;

(c) The peptide-resin was further washed by N-methylpyrrolidine (NMP) and then methanol;

(d) 4 fold molar of Fmoc-amino acid and were activated by 4 fold molar of o-benzotriazole-N,N,N',N'-tetramethyluronium hexafluorophosphate (FBTTU)/hydroxybenzotriazole (HOBT) at room temperature for 20–30 minutes;

(e) The activated Fmoc-amino acid was coupled with the peptide-resin at room temperature for 2–3 hours;

(f) The Fmoc-amino acid-coupling peptide-resin was rinsed with N-methylpyrrolidine (NMP);

(g) The steps (b) to (f) were repeated until a desired peptide was produced.

(h) After the desired peptide was completely coupled to the resin, the bond between the peptide and the resin was cleaved by trifluoroacetic acid (TFA) for 2.5 hours to liberate the peptide.

Various Fmoc-amino acids (Advanced ChemTec, Louisville, Ky. USA) were added to the solid support in the following order to produce the present peptide.

| Serial No. | Fmoc-amino acid | Serial No. | Fmoc-amino acid |
|---|---|---|---|
| 1 | Fmoc-Gly | 8 | Fmoc-Ser |
| 2 | Fmoc-Cys | 9 | Fmoc-Asn |
| 3 | Fmoc-Gly | 10 | Fmoc-Asn |
| 4 | Fmoc-Glu | 11 | Fmoc-Ala |
| 5 | Fmoc-Lys | 12 | Fmoc-Ser |
| 6 | Fmoc-Val | 13 | Fmoc-Pro |
| 7 | Fmoc-Thr | 14 | Fmoc-Cys |

After the designed sequence of peptide I was completely coupled to the solid support, the peptide-resin was treated with trifluoroacetic acid to cleave the linkage between the peptide and the resin in order to liberate the synthesized peptide. The side-chain protecting groups of amino acids which are blocked during synthesis are also cleared from the peptide simultaneously. The resulting peptide was analyzed and purified by reverse phase high performance liquid chromatrography (HPLC) and the amino acid sequence of the peptide was determined by protein sequencer.

The procedures of solid phase synthesis were as follows:

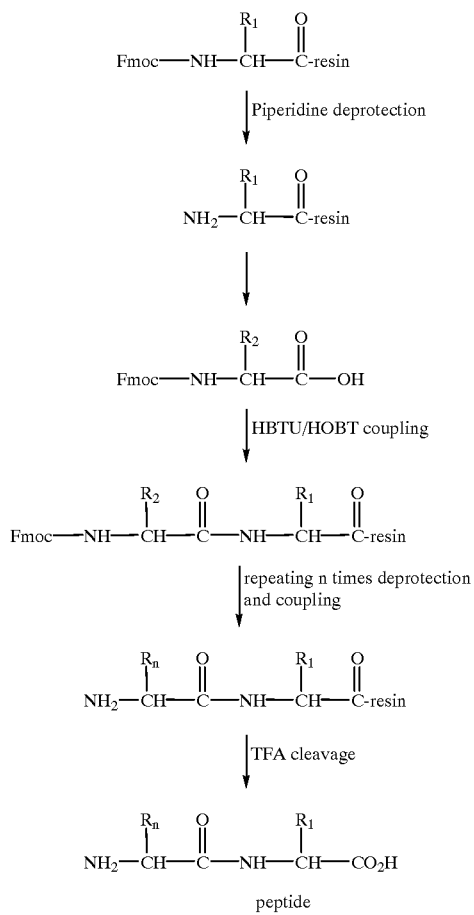

The reverse phase HPLC conditions were as follows:

| | |
|---|---|
| Buffer A: | 0.1% TFA/deionized water |
| Buffer B: | 0.1% TFA/CH$_3$CN |
| Gradient Elution: | 20/80 to 58/42 Buffer B/A, 20 minutes |
| Flow rate: | 1.0 ml/min |
| Detecting wavelength: | 214 mn |
| Column: | Intersil ODS-2 C-18 column, 250 × 4.6 mm |
| Retention time (RT): | 17.6 minutes |

The synthesized peptide I was sequenced by ABI 470 A protein sequencer.

Example 2 The Solid Phase Synthesis of Other Peptides of the Present Invention Peptides II, III and IV were prepared by the procedures of the solid phase peptide synthesis as described in Example 1. While peptides II and III were obtained respectively by deleting a segment of Ser-Thr-Val and a segment of Ser-Thr-Val-Lys-Glu from the C-terminal of peptide I, peptide IV was obtained by deleting a segment of Pro-Ser-Ala-Asn-Asn from the N-terminal of peptide I. The amino acid sequences for each peptide were as follows:

| | |
|---|---|
| Peptide II | CPSANNSTGCG(SEQ ID NO: 6) |
| Peptide III | CPSANNGCG(SEQ ID NO: 7) |
| Peptide IV | CNSTVKEGCG(SEQ ID NO: 8) |

A negative control, i.e. peptide V, was synthesized from a peptide corresponding to a different olfactory receptor protein.

Peptide V CRPKALSAFDTNKGCG (SEQ ID NO:9)

Example 3 The Coating of Peptide I on the Surface of a Piezoelectric Crystal The Surface Treatment of a Piezoelectric Crystal
(1) The electrode for the piezoelectric crystal (Tai-Tien company, ATcut, 9 MHz) was silver which was first rinsed with 95% ethanol and distilled water and then dried in an oven at 100° C. for 30 minutes.
(2) The silver electrode was electric coated with gold at 3.1 voltages for 20 seconds to give a gold electrode.
(3) The gold electrode was immersed in 1.2 N NaOH$_{(aq)}$ for 20 minutes, washed with distilled water and then immersed in 1.2N HCl for 5 minutes after the electrode was rinsed with distilled water and dried in an oven at 100° C. for 16 hours. After cooling, the surface of the electrode was hydrophobic and the frequency of the electrode was measured.

Coating Method
(1) Peptide I was dissolved in water/absolute ethanol (V/V 1/3) solution at a concentration of 2.5 mg/ml.
(2) 0.5 μl of the resulting peptide solution was dropped on one side of the gold electrode via a syringe and the solution was evenly spread over the electrode surface and then dried in air. The other side of the electrode was subjected to the same procedures. In this way the preparation of the peptide I±probe was completed.
(3) The resulting peptide I probe was stored under a vacuum environment.

Example 4 A Comparison of Different Peptides for the Abilities of Detecting Trimethylamine The sensing method described by Wu and Wan et al. (Wu T. Z. and Wan H. H. 1991, Analytical Sciences Vol. 7, Supplement pp. 867–870) was used. The detailed procedures were as follows:

The sensing device is shown in FIG. 1. The piezoelectric crystal coated with the present peptide was inserted into a base plate and covered with a glass shield. The capacity of the glass shield was about 75 cm$^3$. Two μl of the solution to be tested was injected into an evaporating membrane by a syringe. After the solution evaporated and diffused toward the electrode surface at 25° C., the vibration frequency of the piezoelectric crystal electrode was detected by a resonance frequency meter (Smell Company Modles SB02-1 and SB02-2) in an oscillating circuit. The detected frequency data was input into a personal computer for processing the data. After one solution had been tested, the glass shield was removed to release the adsorbed gas from the electrode and the piezoelectric crystal electrode was covered again by a glass shield containing a silica gel desiccant therein to adsorb the moisture adsorbed on the electrode surface. Another solution to be tested was subjected to the detection.

The solutions to be tested included deionized water which was purified by Kintech column, 12.5 wt % aqueous trimethylamine solution (Aldrich Company) and 25 wt % aqueous ammonia solution (Aldrich Company). The evaporating membrane was a cleaning paper (Scott Company) which had been dried in an oven at 120° C. for 12 hours.

The vibration frequency of a piezoelectric crystal electrode which was not coated with the peptide was determined in the gas sensoring device under an environment devoid of moisture, i.e. under the coverage of a glass shield containing the desiccant therein. The determined frequency is recorded as a base frequency and as a blank control. When the piezoelectric crystal possessing a stable base frequency, the piezoelectric crystal electrode to be coated with a peptide to identify various gases. The vibration frequency of a piezoelectric crystal electrode coated with peptide was determined as above-mentioned. The difference (dF) between the vibration frequency of the coated and uncoated electrodes expressed the amount of peptide coated on the electrode and is a reference index for the detection of gas.

Figure 2:
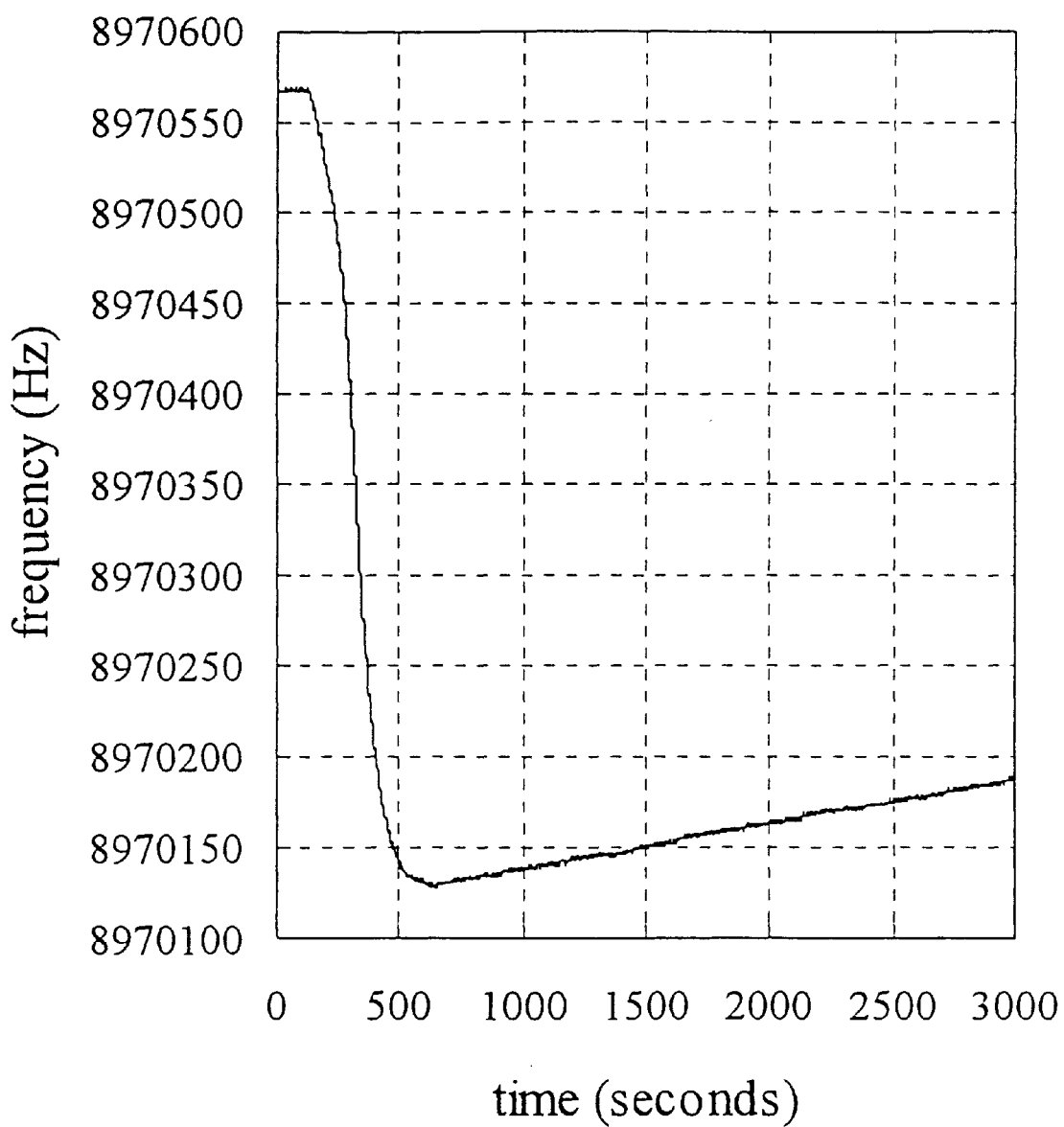
FIG. 2 is a curve showing the response of trimethylamine (TMA) gas using Peptide I as a detector.
Figure 3:
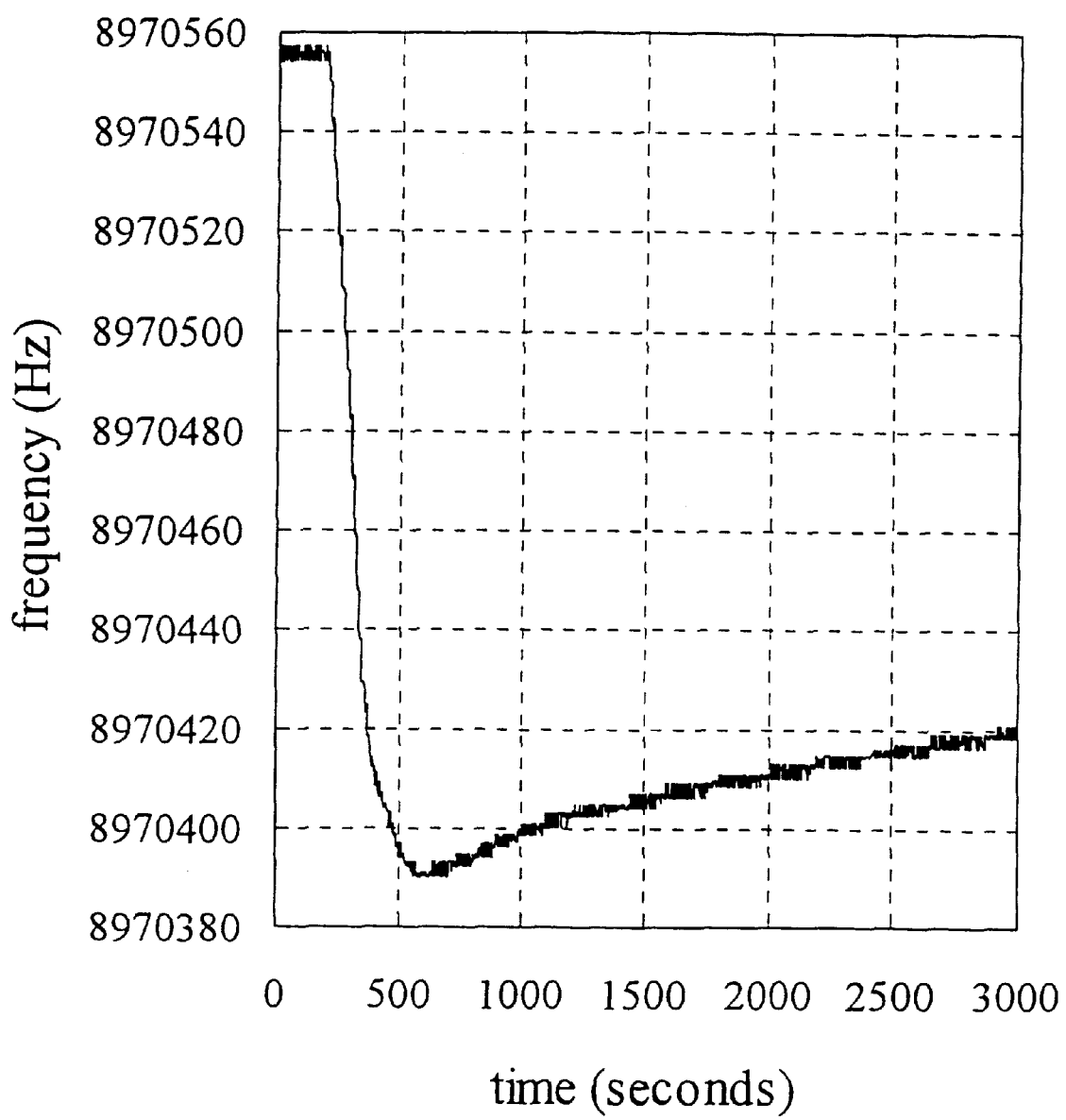
FIG. 3 is a curve showing the response of ammonia ($NH_3$) gas using Peptide I as a detector.
Figure 4:
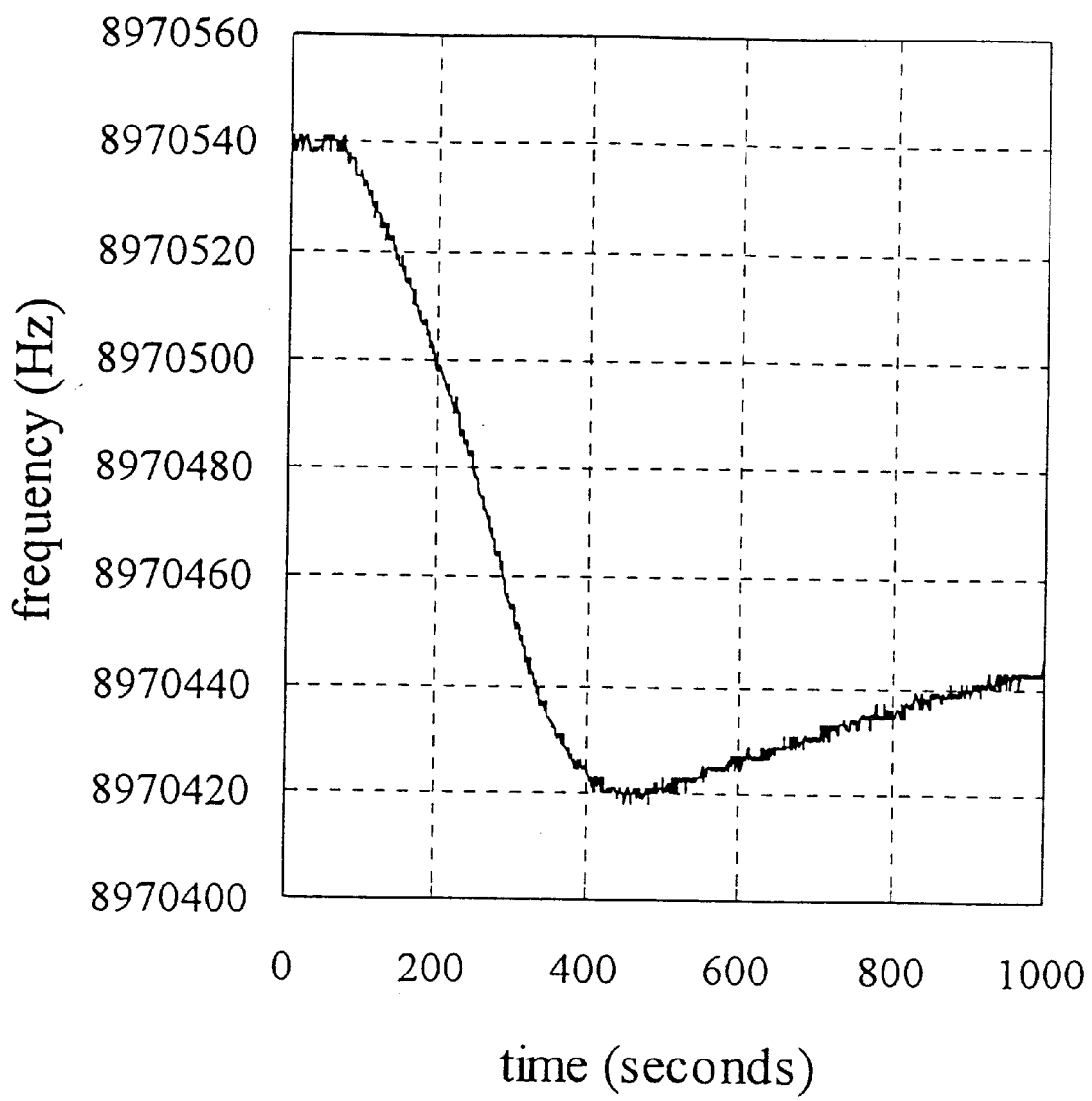
FIG. 4 is a curve showing the response of water ($H_2O$) vapor using Peptide I as a detector.

As a tested solution evaporated and diffused toward the piezoelectric crystal electrode and bound to the peptide coated on the electrode, the load of the electrode increased resulting in the decrease of the vibration frequency of the electrode. FIGS. 2, 3 and 4 show the response curves of peptide I coated on the electrode for detecting trimethylamine gas, ammonia gas and water vapor, respectively. Before injection of the sample, the response curve shows steady which indicates the stability of the frequency of the probe coated with the peptide I. The frequency at that time is a base frequency of the sensor probe. A base frequency is varied with the nature of the crystal and the amount of the peptide and the coating method thereof. When a gas diffuses to the crystal surface and is adsorbed thereon, the load on the crystal increases and results in the gradually decrease of the vibration frequency. The time it takes to attain the minimum frequency is about 5 minutes. The dF value of a tested solution is obtained by subtracting the minimum frequency from the base frequency.

After one test, a desorption of the tested gas from the electrode was carried out by covering it with a clean glass shield containing desiccant. During the desorption, the gas adsorbed on the electrode surface gradually releases, the load of the electrode decreases and the vibration frequency of the electrode gradually recovers to the base frequency. Usually, the frequency of the sensor probe will recover to the base frequency within about 5 minutes.

Generally, the greater the dF value of the coated peptide and the greater the coating amount thereof, the greater the response of the peptide to a tested gas. Thus, the dF value of a tested gas divided by the dF value of the coated peptide gives a normalized dF value of the tested gas. Such a normalized dF value is used to determine the adsorption selectivity of a peptide to a gas.

Figure 6:
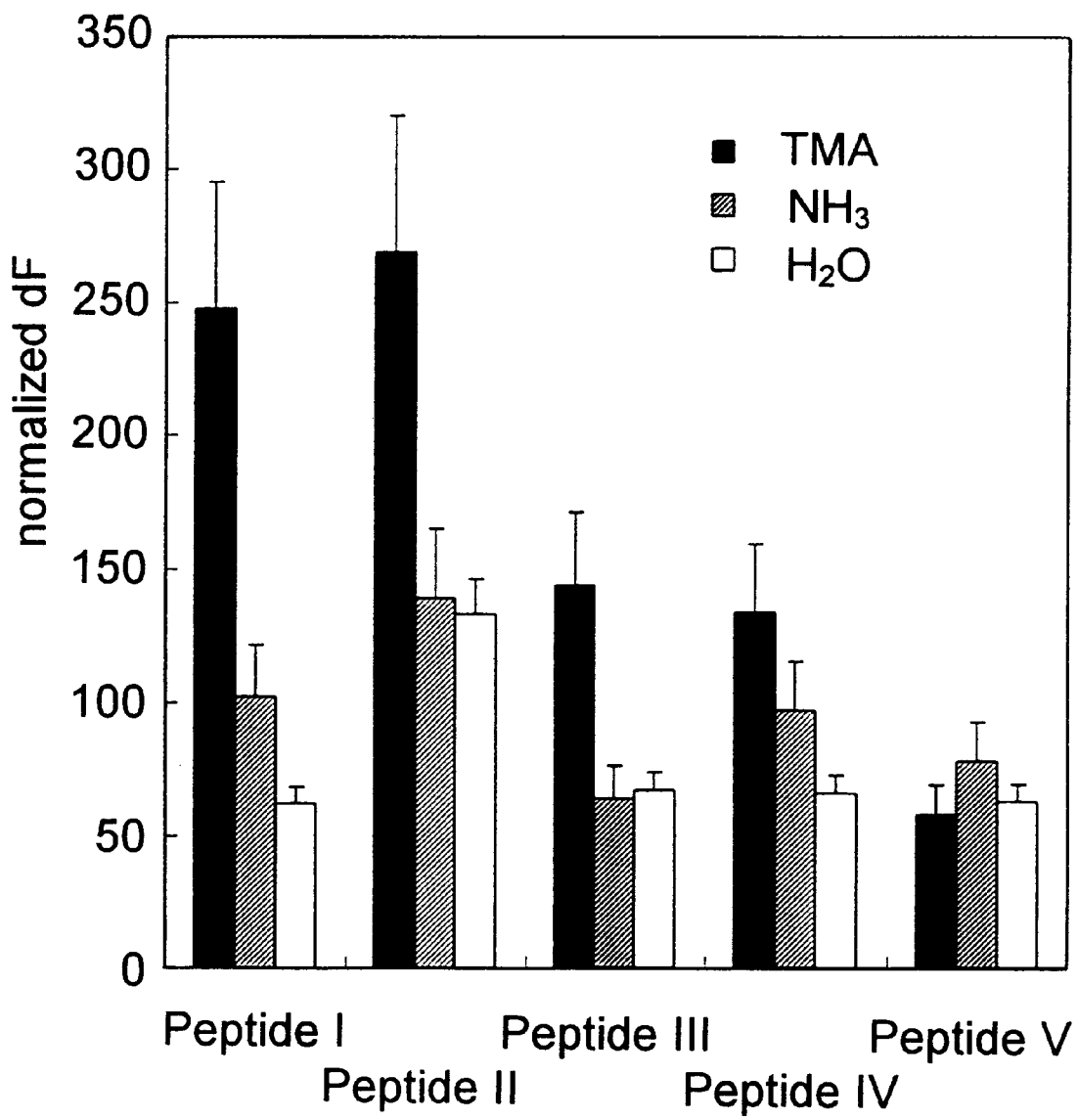
FIG. 6 is a normalized dF showing the responses of three gases (trimethylamine gas, ammonia gas and water vapor) using Peptides I, II, III or IV as a detector.

FIG. 5 and Table 1 clearly show that the probe coated with peptide I has a significant adsorption selectivity to trimethylamine (the number of tested probes is eighteen). If other gases are used as interference gas, the adsorption response of the probe coated with peptide I to trimethylamine is 2.5, 4 and 6 times higher than that of ammonia, water vapor and acetic acid, respectively (the numbers of tested probes for the latter three gases were eighteen, eighteen and twelve, respectively). The adsorption response of the probe coated with peptide I to trimethylamine is 25 times higher than that of aromatic, aliphatic hydrocarbon, acetone, ethyl acetate and ethanol. The comparison of the ability of adsorption of trimethylamine between peptide II, III, VI and V is shown in FIG. 6 and Table 2.

TABLE 2

Normalized dF of Peptides I, II, III, IV and V to Water Vapor Trimethylamine and Ammonia Gas

| | Normalized dF | | | | |
|---|---|---|---|---|---|
| Gas | Peptide I(n = 18) | Peptide II(n = 6) | Peptide III(n = 6) | Peptide IV(n = 6) | Peptide V(n = 6) |
| H2O | 61 ± 110 | 133 ± 25 | 67 ± 5 | 66 ± 3 | 63 ± 6 |
| Tri-methyl-amine (TMA) | 248 ± 53 | 269 ± 23 | 144 ± 14 | 134 ± 10 | 58 ± 8 |
| NH3 | 102 ± 24 | 139 ± 9 | 64 ± 7 | 98 ± 17 | 78 ± 16 | n: the number of tested probes

FIG. 6 shows that each peptide II, III, IV and V has a different adsorption of water vapor, ammonia and TMA gas, respectively. The adsorption of trimethylamine by peptides II, III, VI and V are 2, 2.2, 2 and 0.9) times of those to water vapor, respectively. It is indicated that the deletion of some amino acids from peptide I (i.e. peptides II, III and IV) results in the increase of the amount of adsorbed water. Additionally, the adsorption of water vapor by peptide V is higher than that of trimethylamine.

The adsorptions trimethylamine by peptides II, III, IV and V respectively are 2, 2.2, 1.4 and 0.7 times as compared with those of ammonia, respectively. The results show that the peptides II, III and IV are also selectively binding to trimethylamine, as compared to the control peptide V.

In conclusion, a piezoelectric crystal coated with peptides I, II, III or IV is useful for effectively detecting trimethylamine.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A peptide for detecting trimethylamine, said peptide being selected from the group consisting of:

Cys-Pro-Ser-Ala-Asn-Asn-Ser-Thr-Val-Lys-Glu   (SEQ ID NO.1);

Cys-Pro-Ser-Ala-Asn-Asn-Ser-Thr   (SEQ ID NO.2);

Cys-Pro-Ser-Ala-Asn-Asn   (SEQ ID NO.3);

and a peptide comprising the amino acid sequence

Cys-Asn-Ser-Thr-Val-Lys-Glu   (SEQ ID NO.4).

2. A peptide which detects trimethylamine and binds to a piezoelectric crystal, wherein the peptide comprises a peptide selected from the group consisting of:

Cys-Pro-Ser-Ala-Asn-Asn-Ser-Thr-Val-Lys-Glu-Gly-Cys-Gly   (Peptide I, SEQ ID NO.5);

Cys-Pro-Ser-Ala-Asn-Asn-Ser-Thr-Gly-Cys-Gly   (Peptide II, SEQ ID NO.6);

Cys-Pro-Ser-Ala-Asn-Asn-Gly-Cys-Gly   (Peptide III, SEQ ID NO.7); and

Cys-Asn-Ser-Thr-Val-Lys-Glu-Gly-Cys-Gly   (Peptide IV, SEQ ID NO.8).

\* \* \* \* \*

SEQUENCE LISTING

<160> NUMBER OF SEQ ID NOS: 9

<210> SEQ ID NO 1
<211> LENGTH: 11
<212> TYPE: PRT
<213> ORGANISM: Homo sapiens

<400> SEQUENCE: 1

Cys Pro Ser Ala Asn Asn Ser Thr Val Lys Glu

```
                        1               5                   10

<210> SEQ ID NO 2
<211> LENGTH: 8
<212> TYPE: PRT
<213> ORGANISM: Homo sapiens

<400> SEQUENCE: 2

Cys Pro Ser Ala Asn Asn Ser Thr
  1               5

<210> SEQ ID NO 3
<211> LENGTH: 6
<212> TYPE: PRT
<213> ORGANISM: Homo sapiens

<400> SEQUENCE: 3

Cys Pro Ser Ala Asn Asn
  1               5

<210> SEQ ID NO 4
<211> LENGTH: 7
<212> TYPE: PRT
<213> ORGANISM: Homo sapiens

<400> SEQUENCE: 4

Cys Asn Ser Thr Val Lys Glu
  1               5

<210> SEQ ID NO 5
<211> LENGTH: 14
<212> TYPE: PRT
<213> ORGANISM: Homo sapiens

<400> SEQUENCE: 5

Cys Pro Ser Ala Asn Asn Ser Thr Val Lys Glu Gly Cys Gly
  1               5                   10

<210> SEQ ID NO 6
<211> LENGTH: 11
<212> TYPE: PRT
<213> ORGANISM: Homo sapiens

<400> SEQUENCE: 6

Cys Pro Ser Ala Asn Asn Ser Thr Gly Cys Gly
  1               5                   10

<210> SEQ ID NO 7
<211> LENGTH: 9
<212> TYPE: PRT
<213> ORGANISM: Homo sapiens

<400> SEQUENCE: 7

Cys Pro Ser Ala Asn Asn Gly Cys Gly
  1               5

<210> SEQ ID NO 8
<211> LENGTH: 10
<212> TYPE: PRT
<213> ORGANISM: Homo sapiens

<400> SEQUENCE: 8

Cys Asn Ser Thr Val Lys Glu Gly Cys Gly
  1               5                   10
```

```
<210> SEQ ID NO 9
<211> LENGTH: 16
<212> TYPE: PRT
<213> ORGANISM: Homo sapiens

<400> SEQUENCE: 9

Cys Arg Pro Lys Ala Leu Ser Ala Phe Asp Thr Asn Lys Gly Cys Gly
 1               5                  10                  15
```